(12) United States Patent
Edvardsen et al.

(10) Patent No.: US 9,066,812 B2
(45) Date of Patent: Jun. 30, 2015

(54) OSTOMY APPLIANCE WITH A LEAKAGE INDICATOR

(75) Inventors: Henrik Edvardsen, Copenhagen N (DK); Michael Hansen, Gilleleje (DK); Danuta Ciok, Nivaa (DK); Lene Feldskov Nielsen, Copenhagen K (DK); Kent Hoeier Nielsen, Oelstykke (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/382,526

(22) PCT Filed: Jun. 22, 2010

(86) PCT No.: PCT/DK2010/050152
§ 371 (c)(1),
(2), (4) Date: Feb. 24, 2012

(87) PCT Pub. No.: WO2011/003420
PCT Pub. Date: Jan. 13, 2011

(65) Prior Publication Data
US 2012/0143154 A1    Jun. 7, 2012

(30) Foreign Application Priority Data

Jul. 7, 2009  (DK) ................................. 2009 70055
Jul. 7, 2009  (DK) ................................. 2009 70056

(51) Int. Cl.
| A61M 1/00 | (2006.01) |
| A61F 5/44 | (2006.01) |
| A61B 19/00 | (2006.01) |
| A61F 5/443 | (2006.01) |
| A61F 13/00 | (2006.01) |

(52) U.S. Cl.
CPC ............... *A61F 5/443* (2013.01); *A61F 5/4404* (2013.01); *A61F 2013/00731* (2013.01)

(58) Field of Classification Search
CPC ................................. A61F 13/42; A61L 15/56
USPC ................................................... 604/332–345
See application file for complete search history.

(56) References Cited

U.S. PATENT DOCUMENTS

| 3,941,133 | A | * | 3/1976 | Chen ............................. 604/336 |
| 5,181,905 | A | * | 1/1993 | Flam .............................. 602/41 |
| 5,797,892 | A | * | 8/1998 | Glaug et al. .................. 604/361 |
| 5,942,186 | A |   | 8/1999 | Sanada et al. |
| 6,051,748 | A | * | 4/2000 | Auguste et al. ................ 602/54 |
| 6,171,289 | B1 | * | 1/2001 | Millot et al. .................. 604/336 |
| 7,183,455 | B2 | * | 2/2007 | Utsugi ............................ 602/58 |

FOREIGN PATENT DOCUMENTS

| WO | WO 99/36017 | 7/1999 |
| WO | 07098762 | 9/2007 |

* cited by examiner

*Primary Examiner* — Oren Ginsberg
*Assistant Examiner* — Joshua Lee
(74) *Attorney, Agent, or Firm* — Coloplast Corp., Coloplast A/S; Nick Baumann

(57) ABSTRACT

An ostomy device that comprises an adhesive wafer for attaching to the skin around the stoma. The wafer comprises an adhesive layer having a proximal adhesive surface and a distal surface. The distal surface is covered with a backing layer. The wafer comprises a central portion and a peripheral portion, and it comprises at least a first and a detection zone, wherein the detection zone is configured to provide a tactile sensation on the distal surface of the wafer when exposed to moisture.

20 Claims, 1 Drawing Sheet

OSTOMY APPLIANCE WITH A LEAKAGE INDICATOR

BACKGROUND OF THE INVENTION

1. Field of the Invention

The invention relates to an ostomy appliance with a leakage indicator.

Body attachments for collecting body fluids often have leakage issues. The sources of leakage can be many, for example poor product performance, extended wear time, wrong choice of product for the task, or incorrect application and use. Leakage causes soiled clothes, psychological discomfort and inconvenience, but also more severe issues like infections and skin disorders.

Many products and accessories intended for collecting body fluids are available, and the selection of the right combination for the individual solutions can in many cases reduce the likelihood of leakage.

Devices with electronic leakage detection enable various advanced and complex solutions, however in terms of production costs, user interface complexity, regulatory complexity and the environmental issues related to disposal of electronic components that are integrated in disposable collecting devices, they are not optimal solutions.

2. Description of the Related Art

Different ways of detecting leakage or indicating time for change of the collecting device have been seen in prior solutions.

U.S. Pat. No. 5,942,186 discloses an adhesive plate with an indicator function, and an indicator therefore. The indicator is a hydrophilic composition that contains a water-soluble colouring matter, such as a food colour, a dye, a pigment or metallic salt applied onto or embedded in a part or the whole of a peripheral region of the plate that is spaced apart from the centre thereof. The water-soluble colouring matter is dissolvable in liquid excrements or exudates. It changes colour and provides visible indication of the end of the usable life of the adhesive plate.

EP1 991 187 discloses a method for detecting detachment of a dressing, which is applied to a surface of an at least partly electrically conductive object. The dressing comprises an adhesive for attaching the dressing to the electrically conductive object and at least two electrodes arranged in a distance from the electrically conductive object. A voltage is applied to the first and second electrode establishing an electrical circuit comprising a first capacitor between the first electrode and the electrically conductive object, and a second capacitor between the second electrode and the electrically conductive object. The changes of the capacitance between at least one of the first and the second electrode, and the electrically conductive object are detected, and an alarm is activated when the changes of the capacitance reach a predetermined value.

However there is still a need for a device that is capable of indicating leakage of an ostomy device in a simple and discrete manner.

BRIEF DESCRIPTION OF THE DRAWINGS

The invention is disclosed in more detail with reference to the drawings in which.

DETAILED DESCRIPTION OF THE PRESENT INVENTION

Figure 1:
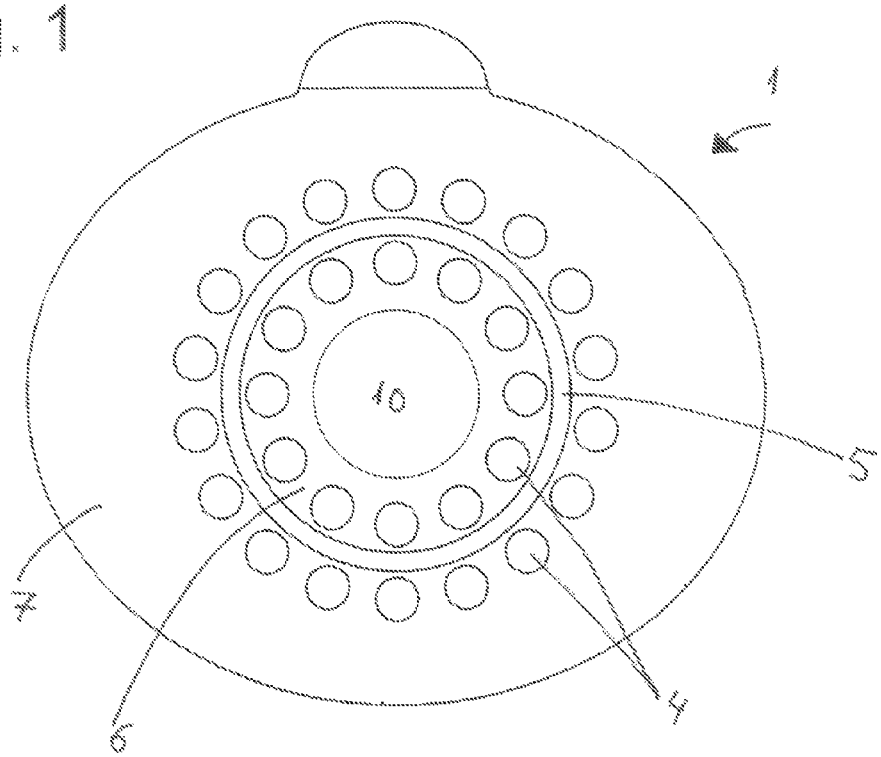
FIG. 1 shows a top view of a preferred embodiment of the invention.

The invention relates to an ostomy device comprising an adhesive wafer for attaching to the skin around the stoma, the wafer comprising an adhesive layer having a proximal adhesive surface and a distal surface, the distal surface being covered with a backing layer, the wafer comprising a central portion and a peripheral portion, the wafer comprising at least one detection zone, wherein the detection zone is configured to provide a tactile sensation on the distal surface of the wafer when exposed to moisture.

By "proximal" is here meant the portion closest to the skin, whereas by "distal" is meant the portion facing away from the skin.

By having a zone on the wafer responding to exposure to moisture by producing a perceivable change, a tactile leakage indicator is present. The tactile indicator is discrete for the user, because it can be felt through clothes and/or the collection bag, and the user can control the leak status without exposing the device.

The device of the invention provides a simple and effective indication of leakage. The device is capable of detecting and indicating leakage occurring underneath the adhesive of the wafer. Because the bag often covers the adhesive wafer when the bag is applied, it is desirable to have indicator means that are not only visual but also monitor leaks in other ways. Electric alarms are known in the art, but are complicated and expensive for use in disposable articles. The tactile indicator of the device of the invention can easily be felt by the fingers or hand of the user and can therefore be checked discretely. The tactile indicator is in the form of at least one detection zone on the adhesive wafer which responds when exposed to moisture by a change in thickness and/or softness, thus providing a tactile sensation on the distal surface of the wafer.

If the detection zone changes in thickness, due to absorption of moisture, the topography of the distal surface of the wafer is altered, and the change can be perceived when the user touches the surface.

In one embodiment, the softness of the detection zone is altered when exposed to moisture. When softness is altered, the topography of the distal surface of the wafer may not necessarily be altered. But the perception on the distal surface of the detection zone, which is sensed by touching with fingers, may be changed, for example from a hard texture to a soft gel-like texture. By hard is meant substantially not compressible, whereas by soft is meant compressible or gel-like.

The tactile indicator solution does not require the use of electronics, and therefore the regulations and challenges related to this type of solution are not an issue. Furthermore, environmental aspects with regard to disposal of the device are diminished.

The device of the present invention provides the user with an increased feeling of security and will reduce the risks related to leakage. The texture of the detection zone changes when exposed to moisture from leakage and provides a tactile sensation on the distal surface of the wafer, for example in the form of raised and/or softened dots, which are easily perceptible by touch. An easy check of a progressing leakage can thus be performed discretely without removing clothes or exposing the bag/device.

By tactile sensation is meant a change that can be sensed by touch, typically by the fingers or hand. The change may be in the form of a change in the topography of the surface of the wafer, such as raised, lowered or lack of knobs or ridges, or by a change in softness of the detection zone.

The tactile indicator responds to leakage from the stoma and to excessive sweating, causing the detection zone of the adhesive wafer to absorb moisture. This produces a tactile change of the distal surface of the wafer, which indicates to the user that it should be changed.

In the embodiment, the thickness of the detection zone may increase when exposed to leakage.

The detection zone may comprise a component that changes texture when exposed to moisture. Examples of such components are hydrocolloids, superabsorbent fibres, superabsorbent particles, alginates, polysaccharides, foam or mixtures thereof. The component may for example react to exposure of moisture by swelling, collapsing, dissolving or hardening. The reaction may be due to the physical form and/or to the chemical nature of the component.

The adhesive used for ostomy wafers may contain hydrocolloid or other moisture absorbing components. The detection zone may comprise moisture-sensitive component(s) in a form that produces a faster and more distinct reaction to moisture than the adhesive of the wafer, so as to monitor the leakage before the adhesive is affected by it.

In one embodiment, the thickness of the detection zone decreases when exposed to leakage. This may be facilitated by incorporating a component that collapses or dissolves when exposed to moisture.

The change of thickness of the second zone when exposed to moisture should be perceptible, being at least 10%, 20%, 30%, 40%, 50%, 60%, 75% or 100% smaller or larger than the thickness of the second zone when dry.

The detection zone may be thinner than the surrounding portion of the adhesive wafer. When exposed to moisture, it may expand to a thickness larger than the thickness of the surrounding wafer, thus producing an easily perceptible response.

In an embodiment, the detection zone is thicker than or substantially the same thickness, as the thickness of the surrounding adhesive wafer.

By the phrase "central portion" is meant an area at the central portion of the wafer. Central should be interpreted as being in the middle portion of the wafer and not peripheral, but should not necessarily be symmetrically located on the wafer. The phrase "peripheral portion" should here be understood as the portion encircling the central portion. The central portion and the peripheral portion are separated by a portion to which a collection bag is attached or can be attached. During use, the central portion of the wafer will be inside the collection bag, whereas the peripheral portion will be outside the bag.

There may be multiple detection zones and they may be arranged in a pattern.

The detection zone(s) may have different configurations and may be in the form of one or more cohesive zones or multiple discrete zones. They may for example be in the form of one or more concentric circular tracks, or it may be in the form of dots or knobs or lines, arranged randomly or in a pattern. The dots or lines may be aligned on a circular track, concentric to the centre of the wafer. The dots or lines may be raised or embossed.

When the detection zones are arranged in a pattern, it is easy to detect the point of leakage and its progress. An example of such a pattern could be an array of discrete dots facilitating that the dot(s) exposed to moisture from a leakage will be affected, whereas the other dots will not. In this way, it is easy to feel exactly the point of leakage on the wafer and how far it has progressed, and thereby determine when it is time to change the device. The detection zones may be located at the central portion or at the peripheral portion or at both locations, for example by an array of dots at each portion.

The moisture sensitive component of the detection zone may be arranged as at least partly embedded in the adhesive wafer. The component of the detection zone may in one embodiment extend over the entire thickness of the wafer.

In order to make the tactile sensation of the detection zone more distinct, the backing layer of the wafer may be embossed in the detection zone. An example of such embossment may be to create depressions in the distal surface of the wafer. When the component of the zone is exposed to moisture, it swells and expands and turns the embossment "inside-out" to produce a distinct protruding point or ridge at the distal surface.

The backing layer of the wafer may be any suitable layer, such as a polymer film, non-woven foam or a foamed film. The backing layer may be vapour and water impermeable, or it may be water impermeable but vapour permeable.

The detection zone(s) may be provided with a backing layer being more flexible than the backing layer of the wafer. The softer and more flexible backing layer may facilitate more distinct expansion of the detection zones.

Furthermore, the tactile sensation of the detection zones may be supported by or even solely achieved by altering the texture of the backing layer over the detection zone(s). The backing layer may for example be provided with a rugged surface. If the detection zone is thinner than the surrounding wafer before exposure to moisture the rugged surface cannot be felt, but when the detection zone expands, the rugged surface will become accessible and thus perceivable for the fingers.

The ostomy device may further be provided with a visual indicator that produces a change in colour when exposed to moisture. The visual indicator may be integrated in the detection zone or a part thereof, or it may be partly or fully integrated in the adhesive wafer. The visual indicator may be located on the peripheral portion of the wafer for easy visual access.

The visual indicator may respond to presence of moisture, or it may be more specific and only react to for example output from the stoma and not to for example moisture from perspiration. Such differentiation can be achieved by the use of pH-specific indicators or indicators specific to certain enzymes or bacterial components.

In one embodiment, the indicator produces a change in temperature when exposed to moisture and the change may be sensed by the user.

The body attaching wafer of an ostomy device is normally partly hidden by the collecting bag. This makes it difficult for a user to monitor a visual leakage indicator on the wafer. Furthermore, an optimal location of a detection point would be from 1 mm to 25 mm from the edge of the central portion facing the stoma, and this will typically be at the portion of the wafer being inside the bag, and therefore difficult to access visually.

The visual indicator may be provided with a wicking system, where moisture is collected at one or more detection points at the central portion of the wafer, and then transported by a wick to the colour indicator at the peripheral portion of the wafer, producing a visual response here. In this way, the moisture is detected and visualized at an early stage of the leakage. The wick material can be made from a variety of absorbent materials such as non-woven, filter paper, textile, adhesive or super absorbers such as acrylic acids and the like.

The adhesive layer of the wafer may be any suitable skin-friendly adhesive.

The ostomy device may be a one piece device where a collection bag is inseparately attached to the wafer or it may be a two piece device where the wafer and the collection bag are provided with coupling means and can therefore be attached and detached to each others.

DESCRIPTION OF THE EMBODIMENTS

The invention is now explained in more detail with reference to the drawings showing the embodiments.

FIG. 1 shows a view of the distal surface of a preferred embodiment of the invention.

Figure 2:
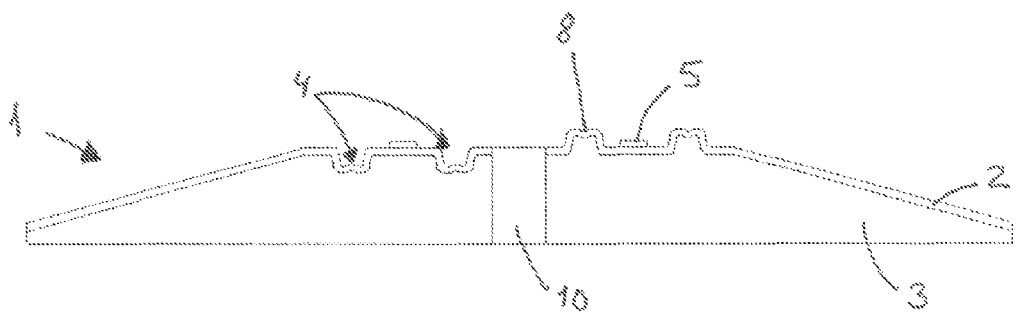
FIG. 2 shows the embodiment in cross-section.

FIG. 2 shows the same embodiment in cross-section. The device comprises a wafer (1) comprising a backing layer (2) and an adhesive layer (3) and a central hole (10) for accommodating the stoma. The wafer (1) comprises at least one detection zone (4), the detection zone (4) being in the form of embossed portions having a smaller thickness than the surrounding adhesive wafer. The portion (5) for attaching a collection bag (for clarity reasons, the bag is not shown in the figures) separates the central portion (6) and the peripheral portion (7). When exposed to moisture from leakage, the depressed portions of the detection zone (4) will expand, and the zones (4) will raise to a thickness that is at least the same as the surrounding adhesive wafer and may raise to a thickness larger than the thickness of the wafer thus providing raised dots on the distal surface of the wafer (1). Only the leakage area is affected, so it is easy for the user to feel the extent of the leak as well as the location of it. FIG. 2 shows a limited leakage, where some of the detection zone dots are raised into protruding knobs (8). Those detection zone dots (4) that are not exposed to the leakage are not raised.

The invention claimed is:

1. An ostomy device comprising:
   an adhesive wafer for attaching to skin around a stoma, the wafer including:
      an adhesive layer having a proximal adhesive surface and a distal surface;
      a backing layer, wherein the backing layer is water impermeable and covers the distal surface;
      a central portion surrounding a central hole; and
      a peripheral portion surrounding the central portion,
      wherein at least one of the central portion and the peripheral portion includes at least one detection zone, the detection zone including:
         at least one embossed portion having a smaller thickness before exposure to moisture than a thickness of the detection zone adjacent to the embossed portion, and having a greater thickness after exposure to moisture than the thickness of the detection zone adjacent to the embossed portion for providing a tactile sensation.

2. The ostomy device according to claim 1, wherein the detection zone is configured to provide the tactile sensation through the water impermeable backing layer on the distal surface when exposed to moisture.

3. The ostomy device according to claim 1, wherein the thickness of the embossed portion increases at least 10% when exposed to moisture.

4. The ostomy device according to claim 1, wherein there are multiple detection zones.

5. The ostomy device according to claim 4, wherein the detection zones are disposed on a circular track.

6. The ostomy device according to claim 1, the detection zone surrounds the central hole.

7. The ostomy device according to claim 1, wherein the detection zone is formed as a discrete dot.

8. The ostomy device according to claim 1, wherein the detection zone includes a component that expands when absorbing moisture.

9. The ostomy device according to claim 8, wherein the component is selected from the group consisting of hydrocolloids, superabsorbent fibres, superabsorbent particles and foam.

10. The ostomy device according to claim 1, wherein the at least one of the central portion and the peripheral portion further includes a second detection zone that includes a component that changes in softness when absorbing moisture.

11. The ostomy device according to claim 1, wherein the detection zone is disposed in the central portion.

12. The ostomy device according to claim 1, wherein the detection zone is disposed in the peripheral portion.

13. The ostomy device according to claim 12, wherein the peripheral portion further includes a visual indicator, wherein the visual indicator produces a change in color when exposed to moisture.

14. The ostomy device according to claim 13, wherein the visual indicator changes color only when exposed to moisture that is within a pre-defined pH range.

15. The ostomy device according to claim 14, wherein the visual indicator changes color only when exposed to moisture containing a particular enzyme or bacterial component.

16. The ostomy device according to claim 1, further including a portion configured for attaching a collection bag, wherein the portion configured for attaching a collection bag separates the central portion and the peripheral portion.

17. The ostomy device according to claim 1, wherein each of the central portion and the peripheral portion includes at least one detection zone, the detection zone including:
   at least one embossed portion having a smaller thickness before exposure to moisture than a thickness of the detection zone adjacent to the embossed portion, and having a greater thickness after exposure to moisture than the thickness of the detection zone adjacent to the embossed portion for providing a tactile sensation.

18. An ostomy wafer comprising:
   an adhesive layer having a distal surface attached to a water impermeable backing layer, and a proximal adhesive surface on a side opposite of the water impermeable backing layer;
   a central portion surrounding a hole that is formed through a wafer thickness of the ostomy wafer, the wafer thickness extending between the water impermeable backing layer and the proximal adhesive surface measured at the hole;
   a peripheral portion surrounding the central portion; and
   at least one detection zone formed as an indent in the ostomy wafer;
   wherein the detection zone has a smaller thickness before exposure to moisture than the wafer thickness, and greater thickness after exposure to moisture than the wafer thickness.

19. The ostomy wafer according to claim 18, wherein there are multiple detection zones.

20. The ostomy wafer according to claim 18, wherein the detection zone is configured to provide a tactile sensation through the water impermeable backing layer on the distal surface when exposed to moisture.

* * * * *